United States Patent [19]

Atake

[11] Patent Number: 4,780,833
[45] Date of Patent: Oct. 25, 1988

[54] SYSTEM FOR MEASURING LIQUID

[76] Inventor: Minoru Atake, 579-6, Ohoiso, Ohoisa-machi, Kanagawa-Ken, Japan

[21] Appl. No.: 813,623

[22] Filed: Dec. 26, 1985

[30] Foreign Application Priority Data

Sep. 17, 1985 [JP] Japan .................. 60-206028

[51] Int. Cl.⁴ ............... G06F 3/05; B65B 3/04
[52] U.S. Cl. .................... 364/509; 364/558; 73/864.14; 73/864.15
[58] Field of Search ......... 364/479, 558, 564, 509, 364/562, 497; 73/303, 864.11, 864.14, 864.15, 863.02, 864.24; 141/267

[56] References Cited

U.S. PATENT DOCUMENTS

| | | | |
|---|---|---|---|
| 3,963,061 | 6/1976 | Kenney | 73/864.14 |
| 4,369,664 | 1/1983 | Bunce et al. | 73/864.11 |
| 4,422,151 | 12/1983 | Gilson | 364/479 |
| 4,586,546 | 5/1986 | Mezei et al. | 73/864.24 |
| 4,671,123 | 6/1987 | Magnussen, Jr. et al. | 73/864.14 |

Primary Examiner—P. S. Lall
Assistant Examiner—David Goldman
Attorney, Agent, or Firm—Frishauf, Holtz, Goodman & Woodward

[57] ABSTRACT

A system for measuring liquid comprises means for applying suction to liquid to be measured, means for maintaining liquid in a micro-pipette tube or tubes, said tube having a storage portion with a large inner diameter and a slender tubular portion with small diameter, and a pressure gauge for measuring potential head in said micro-pipette tube or tubes.

15 Claims, 3 Drawing Sheets

SYSTEM FOR MEASURING LIQUID

BACKGROUND OF THE INVENTION

The present invention relates to a system for measuring liquid and more particularly to a system for detecting whether or not a micro-pipette tube or tubes be in accord with a prescribed value by measuring a liquid height in the micro-pipette tube or tubes when air suction is applied to the micro-pipette tube or tubes.

In a case that test liquid material e.g. sera is divided into a plurality of test tubes for intensive investigation, it is necessary to monitor whether or not the test material is divided into uniform, regulated volumes.

Generally, the volume of the test material was detected directly by scale of the pressure gauge which is in proportion to a hydraulic head, when the air suction is applied to the micro-pipette tube or tubes. Accordingly, the prior art system is incapable of analysis precision below 1 millimeter readable to a liquid height or level in the micro-pipette tube or tubes. Such a reading is within the measuring error of the pressure gauge and is unreliable.

SUMMARY OF THE INVENTION

An object of this invention is to provide a reliable system for measuring liquid with a higher precision although a pressure gauge directly indicates a hydraulic head in proportion to a liquid level or height in a micro-pipette tube or tubes.

Therefor, a measuring system according to this invention includes a special micro-pipette tube or tubes, said tube having a storage portion with a large inner diameter and a slender tubural portion with small diameter impervious to air displacement.

Another object of this invention is to provide a reliable system for measuring liquid with a higher precision as added by detecting scale of the pressure gauge particularly in the best timing in which the pressure gauge accurately indicates a liquid volume.

BRIEF DESCRIPTION OF THE DRAWINGS

Other object of this invention will be readily understood from the following description with reference to the accompanying drawings as follows.

DESCRIPTION OF THE PREFERRED EMBODIMENTS

Figures 1, 6:
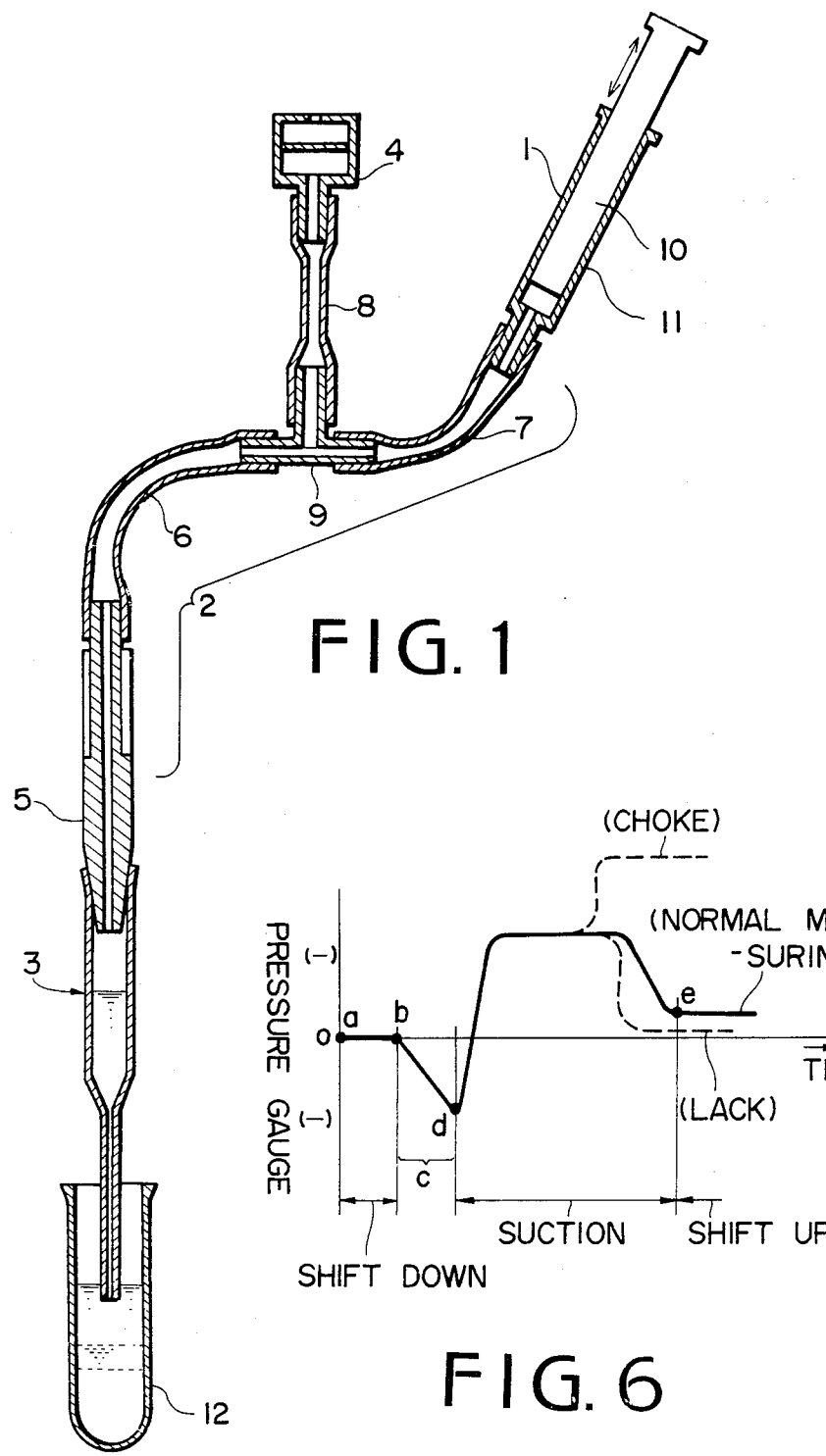
FIG. 1 is a vertical cross-section of a system according to one embodiment of this invention.
FIG. 6 is a time diagram depicting pressure indicated by a pressure gauge in the embodiment of FIG. 5.
Figure 2:
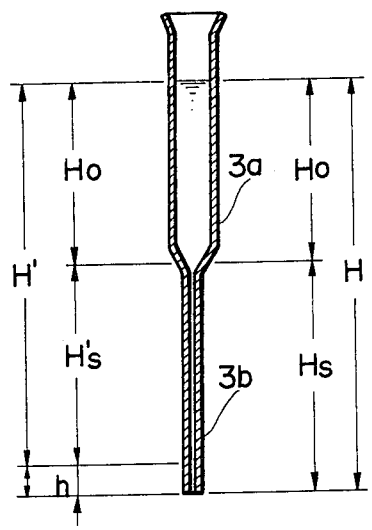
FIG. 2 is a vertical cross-section of a pipette including references used to explain the measure of liquid level.
Figure 3:
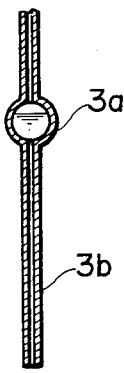
FIG. 3 is a vertical cross-section of a pipette modified from that of the embodiment mentioned above.

As shown in FIGS. 1 to 3, a system for measuring liquid level according to this invention includes means 1 for applying suction to the liquid to be measured, means 2 for maintaining the liquid in a pipette tube 3, and a pressure gauge 4 for measuring a potential hydraulic head in the pipette tube 3.

In this embodiment, the means 1 is a piston-cylinder assembly and the means 2 further includes a connector 5 having a tapered lower end portion to which the pipette tube 3 is detachably connected, flexible tubes 6, 7 and 8, and a T-joint 9. The piston-cylinder assembly 1 includes a piston 10 which is operated by means of an actuator as mentioned hereinafter, and a cylinder 11 having a joint portion.

In order to communicate the micro-pipette tube 3 with the piston cylinder assembly 1 and pressure gauge 4, the connector 5 joins to T-shaped joint 9 via the flexible tube 6, and the joint 9 joins to the joint portion of the cylinder 11 via the flexible tube 7 and to the pressure gauge 4 via the flexible tube 8.

The pipette tube 3 comprises a storage portion 3a having a large inner diameter, for example, of 5 mm and a slender tube portion 3b having a small inner diameter, for example, of 0.5 mm which is impervious to air displacement. Namely, in the slender tube portion, the liquid can not be displaced by air or gas due to its condensability. Accordingly, in this example, the inner cross-section A of the storage portion 3a in proportion to the inner cross-section a of the slender tube portion 3b is equal to 100 fold ($A = 100 \times a$).

Figure 4:
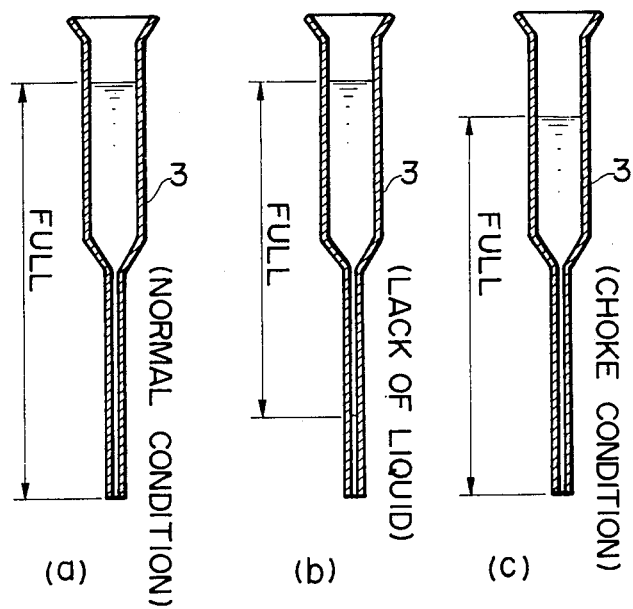
FIGS. 4(a) to 4(c) are vertical cross-sections indicating conditions of liquid bodies induced into pipette tubes respectively when the suction is applied to the tubes.

In a normal condition, the liquid body is supplied to the storage portion 3a and slender tubural portion 3b of the micro-pipette 3 when the piston-cylinder assembly 1 is so operated as to suck air in the micro-pipette, and the liquid body in the pipette is maintained with its liquid level or height being up to H as shown in FIG. 4(a) when the sucking operation of the piston-cylinder assembly 1 is finished, and the pressure gauge 4 indicates a suitable potential hydraulic head in proportion to the liquid level H.

In order to monitor whether or not liquid material supplied to a container 12 has a prescribed volume, or to divide the liquid material in the test tube into a plurality of containers with its prescribed volume by means of the micro-pipette, this system adapts three steps as follows: Namely, at the first stage, the slender portion of the micro-pipette 3 dips into the liquid in container 12 or test tube with its low end thereof being at the bottom of the container 12 or being maintained to the constant depth of the liquid body in the test tube, then the piston-cylinder assembly 1 is operated to suck air by the prescribed volume according to the piston stroke, and finally, the pipette 3 is lifted upwards from the container 12 or test tube, before the hydraulic head in the pipette is read by the pressure gauge 4.

If the liquid material in the container 12 or test tube is insufficient, the system detects an abnormal condition as shown in FIG. 4(b). Namely, when or before the sucking operation of the piston-cylinder assembly 1 is finished, the liquid body is completely absorbed into the storage portion 3a and slender tubural portion 3b with its liquid level being to H' as shown in FIG. 4(b)(H'≠H), and the pressure gauge 4 indicates an insufficient hydralic head in proportion to the liquid level H'.

In this case, shortage h (h=H−H') can be indicated by the pressure gauge 4 as a reliable value if the shortage h is more than 1 mm which is a limit equal to the measuring error of the pressure gauge 4 as shown in FIG. 3.

In the normal condition, the liquid volume L to be monitored or detected is as follows;

$$L = H_o \times A + H_s \times a = a(100H_o + H_s) \quad (1)$$

in this formula, $H_o$ means a liquid level in the storage portion 3a and $H_s$ means a liquid level in the slender tubural portion 3b.

In the abnormal condition as shown in FIG. 4(b), the liquid volume $L'$ to be monitored or detected is as follows;

$$L' = H'_o \times A + H'_s \times a = a(100H'_o + H'_s) \quad (2)$$

in this formula, $H'_o$ means a liquid level in the storage portion 3a and $H'_s$ means a liquid level in the slender tubural portion 3b. In this case, for example, as $H'_o = H_o$, $H'_s = 0.9H_s$ and $H_o = H_s = >10$ mm are determined or measured, $$\Delta L = L - L' = a(100H_o + H_o) - a(100H_o + 0.9H_o) \quad (3)$$

$$\Delta L/L \approx 0.001 \quad (4)$$

Accordingly, the pressure gauge 4 can indicate one-thousandth of liquid volume in this system as a potential hydraulic head.

An abnormal condition shown in FIG. 4(c) indicates the fact that the micro-pipette 3 is choked by impurity included in the liquid material when or before the sucking operation of the piston cylinder assembly 1 is finished. This condition is converted to the abnormal condition shown in FIG. 4(b), when the pipette 3 is shift upwards from the container 12 or test tube, because the impurity is dropped down and left from the lower end of the slender tubural portion 3b so as to release the choke condition.

In this embodiment, the pressure gauge 4 may be a strain gauge having a diaphragm, and it is necessary to fill the liquid material at least in both storage and slender portions in this system's operation.

Figure 5:
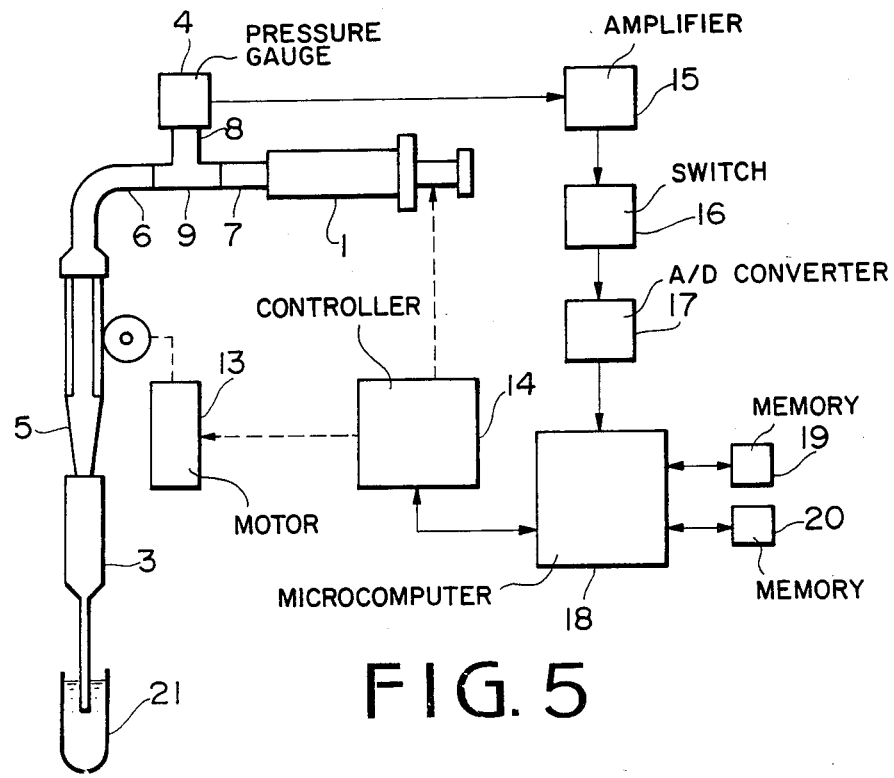
FIG. 5 is a block diagram indicating a system according to another embodiment of this invention.

FIGS. 5 and 6 indicate a system of this invention as an another embodiment. The system further includes an electric motor 13 for shifting the connector 5 together with the micro-pipette tube 3 upwards and downwards, a controller 14 for controlling the drive operation of the motor 13 and operating the piston-cylinder assembly 1 as an actuator, an amplifier 15 adapted to receive from the pressure gauge 4 an electric output signal, a switch device 16 adapted to be operated by a signal supplied via an A/D converter 17 from the pressure gauge 4, and a micro-computer unit 18 adapted to receive the switching signal supplied from the switch device 16 and to write it to memories 19 and hold the reference signal to memory 20, and to supply a control signal to the controller 14.

In the embodiment shown in FIGS. 5 and 6, this system is used so as to divide the liquid material stored in a test tube 21 into a plurality of containers with a prescribed volume.

In operation, the motor 13 is driven by the control signal supplied through the controller 14 from the computer unit 18 so as to shift the pipette tube 3 downwards and into the liquid material in the test tube 21, and simultaneously the switch device 16 puts in a first operation by a signal supplied from the computer unit 18 so as to monitor atmospheric pressure by means of the pressure gauge 4, thereby to cause an electric signal to be supplied to the computor computer unit 18 and to be memorized to the memory 19 under a present control program. This stage is shown in FIG. 6 as point (a).

After the lower end of the slender tubural portion come in contact with the surface of the liquid material in the test tube 21 (point (b) shown in FIG. 6), the pipette tube is shifted down so as to raise the inner pressure slightly. At this time (point (c) shown in FIG. 6), the monitor value detected by means of the pressure gauge 4 is converted to an electric signal and supplied to the computer unit 18 so that the supplied signal is compared with the signal memorized in the memory 19 by means of comparator which is included in the computer unit 18. For example, as the pipette tube 3 is shifted down with the lower end of the slender tube 3b reaching to a depth of 1 to 2 mm (refer (d) point shown in FIG. 6), if a differential value given as result of a comparison between the supplied signal to the signal in the memory 19 is equal to a reference value predetermined and memorized in the memory 20, the computer unit 18 supplies a control signal to the controller 14 so as to drive the piston 10 of the piston-cylinder assembly 1, thereby to cause suction power to be applied to the pipette tube 3. In this time of the suction, the motor is driven in accordance with the decrease of the liquid material in the test tube 21 so as to maintain a suitable depth of the slender tube 3b, and the pressure gauge 4 monitors potential hydraulic head in the pipette tube 3 so as continuously to supply monitor signal to the computer unit 18.

After a time predetermined to the start of the sucking operation, for example, 1 to 2 seconds, the back pressure applied to the suction and hydraulic head detected to the pressure gauge are converged to a static and stable value.

At this stage, the controller 14 stops the piston 10 (point (e) shown in FIG. 6), and drives the motor 13 in reverse rotation by means of a signal supplied from the computer unit 18, thereby to cause the micro-pipette 3 to be shifted upwards and above the liquid material in the test tube 21.

At this time, the computer unit 18 decides whether or not the micro-pipette 3 holds a prescribed and suitable liquid volume based on the monitor information of the pressure gauge.

If the pipette tube 3 is choked due to impurity such as fibrin included in sera, or separator in suction operation, when the suction is finished, the inner liquid level in the micro-pipette tube 3 is low and the back pressure is maintained higher than that in a normal condition and so far and away from the converged static value. When the motor 13 is rotated in reverse, the pipette is shifted upwards, whereby the computer unit 18 decides the liquid material in error division by the monitor information of the pressure gauge 4.

If the pipette tube 3 introduces air into itself during suction, for example, the test tube 21 is emptied before the suction is finished, due to improper operation, the inner liquid level in the pipette tube 3 is high and the back pressure is maintained lower than that in a normal condition and so far and away from the converged static value. When the motor 13 is rotated in reverse, the pipette is shifted upwards, liquid material in error division by monitor information of the pressure gauge 4 is judged because the potential hydraulic head is lower than that of a normal division.

In these embodiments, only one micro-pipette tube 3 is used for the measuring system. However, a plurality of micro-pipette tubes may be applied to one system in order to detect or monitor liquid materials divided in mass production.

What is claimed is:

1. A system for measuring the amount of liquid aspirated into a micro-pipette tube comprising:
   a micro-pipette tube having a storage portion adapted to accommodate aspirated liquid therein and a tubular portion having a tip adapted for insertion into a liquid, the inner cross-section of said tube portion being greatly smaller than the inner cross-section of said storage portion, an end of said tubular portion opposite to said tip being in communication with said storage portion;
   means for applying suction to said storage portion for aspirating liquid thereinto through said tip and said tubular portion, and to maintain such aspirated liquid within the micro-pipette tube;
   a pressure measurement means coupled to the micro-pipette tube for measuring the potential hydraulic head of said aspirated liquid after deactivation of the suction applying means, and to provide a volume indication of the aspirated liquid.

2. The system of claim 1, wherein the cross-section of said storage portion is 100 times greater than the storage portion of said tubular portion.

3. The system of claim 2, further comprising control means for initiating aspiration, said control means including a power means for lowering and raising the micro-pipette tube relative to said liquid to, respectively, insert said tip into and remove it from the liquid.

4. The system of claim 3, wherein said control means comprises a comparator means responsive to the pressure measurement means and a stored signal to generate a difference signal.

5. The system of claim 4, wherein said control means comprises actuator means responsive to said difference signal and a reference signal to actuate said power means to lower said tip into said liquid and begin aspiration.

6. The system of claim 5, wherein said control means removes the tip from said liquid after a predetermined time has elapsed from when aspiration was begun.

7. The system of claim 6, wherein said control means comprises means for determining from said measurement signal whether the micro-pipette tube operation is faulty.

8. The system of claim 9, wherein said determining means is operative to be responsive to said measurement signal only when the tip is removed from the liquid.

9. The system of claim 5, further comprising control means for initiating aspiration, said control means including a power means for lowering and raising the micro-pipette tube relative to said liquid to, respectively, insert said tip into and remove it from the liquid.

10. The system of claim 9, wherein said control means comprises a comparator means responsive to the pressure measurement means and a stored signal to generate a difference signal.

11. The system of claim 10, wherein said control means comprises actuator means responsive to said difference signal and a reference signal to actuate said power means to lower said tip into said liquid and begin aspiration.

12. The system of claim 11, wherein said control means removes the tip from said liquid after a predetermined time has elapsed from when aspiration was begun.

13. The system of claim 12, wherein said control means comprises means for determining from said measurement signal whether the micro-pipette tube operation is faulty.

14. The system of claim 5, wherein said control means comprises means for determining from said measurement signal whether the micro-pipette tube operation is faulty.

15. A method for measuring the amount of liquid aspirated into a micro-pipette tube comprising the steps of:
   aspirating liquid into a micro-pipette tube;
   retaining such aspirated liquid in said micro-pipette tube;
   removing the micro-pipette tube from the liquid;
   measuring the potential hydraulic head of said aspirated liquid to generate a measurement signal; and
   determining the amount of said aspirated liquid from said measurement signal.

* * * * *